United States Patent
Branemark

[11] Patent Number: 5,108,444
[45] Date of Patent: Apr. 28, 1992

[54] SYSTEM FOR RECONSTRUCTING THE DISTAL RADIOULNAR JOINTS (DRU-JOINTS) IN WRISTS

[76] Inventor: Per-Ingvar Brånemark, Andergatan 3, S-431 69 Mölndal, Sweden

[21] Appl. No.: 630,518
[22] Filed: Dec. 20, 1990

[30] Foreign Application Priority Data

Apr. 26, 1990 [SE] Sweden .................. 9001520

[51] Int. Cl.⁵ .............................. A61F 2/42
[52] U.S. Cl. .................................... 623/21
[58] Field of Search ................ 623/21, 16, 18

[56] References Cited

U.S. PATENT DOCUMENTS

| | | | |
|---|---|---|---|
| 3,909,853 | 10/1975 | Lennox | 623/21 |
| 4,040,130 | 8/1977 | Laure | 623/21 |
| 4,063,314 | 12/1977 | Loda | 623/21 |
| 4,224,695 | 9/1980 | Grundei et al. | |
| 4,229,840 | 10/1980 | Gristina | 623/21 |
| 4,229,841 | 10/1980 | Youm et al. | 623/21 |
| 4,307,473 | 12/1981 | Weber | 623/21 |

FOREIGN PATENT DOCUMENTS 0127503 12/1984 European Pat. Off. .
568066 10/1975 Switzerland .

*Primary Examiner*—David J. Isabella
*Attorney, Agent, or Firm*—Ostrolenk, Faber, Gerb & Soffen

[57] ABSTRACT

A system for reconstructing the distal radioulnar joint (DRU-joint) in the wrist. The system includes as a substantial component a guide body (3) anchorable to the radius (1) and having a guide slot (14) with a control element (8) extending into the guide slot (14) and adjustably secured in the ulna (2).

22 Claims, 2 Drawing Sheets

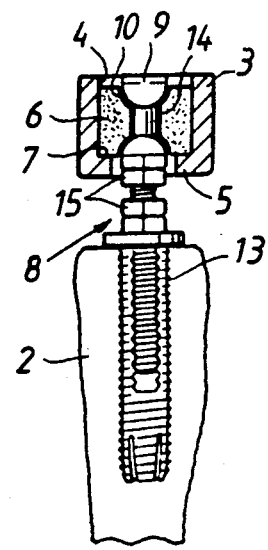
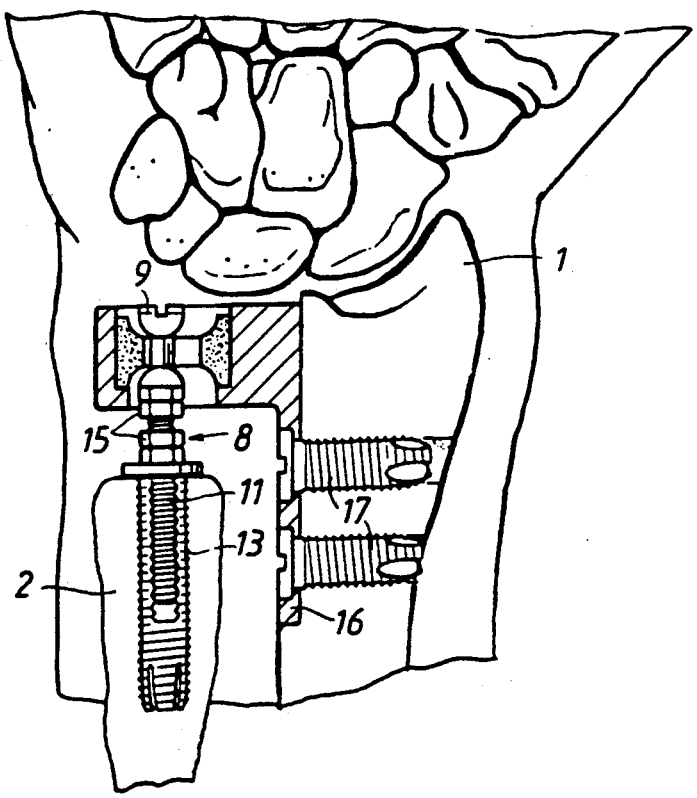

SYSTEM FOR RECONSTRUCTING THE DISTAL RADIOULNAR JOINTS (DRU-JOINTS) IN WRISTS

BACKGROUND OF THE INVENTION

1. Field of the Invention

The present invention relates to a system for reconstructing the distal radioulnar joints (DRU-joints) in wrists.

2. Background Prior Art

The DRU-joint is necessary to provide the wrist with sufficient lateral flexibility. The relevant pivot or rotation here is approximately ±90°, i.e. 180°, and is entirely decisive to the function of the wrist.

No constructions have hitherto been achieved to replace this joint function in a defective DRU-joint.

SUMMARY OF THE INVENTION

It has now surprisingly proved possible, for the first time, to solve this problem by means of the system proposed according to the invention.

The present invention concerns a system for reconstructing the distal radioulnar joint (DRU-joint) in the wrist. A guide body is anchorable to the radius bone. The guide body includes a guide slot which is above and which opens toward the ulna beneath the guide body. A control element extends through the guide slot and is adjustably securable in the ulna. An insert may be positioned in the bore hole of the guide body and that insert abuts the bottom or end flange of the guide body. Preferably, the height of the insert is less than the height of the bore hole of the guide body. The guide slot in the guide body is preferably a slot-shaped guide in the insert within the body. The guide slot of the guide body and of the insert is shaped to provide sufficient clearance for the control element secured in the ulna as to permit the guide body to move with respect to the control element at the wrist.

The invention will be described in more detail in the following with reference to an embodiment illustrated in the accompanying drawings in which

BRIEF DESCRIPTION OF THE DRAWING

FIGS. 2 and 3 respectively show an exploded view and a side view (partly in cross-section) of the main components of the DRU-joint reconstruction according to the invention, and FIG. 4 shows a diagrammatic sketch (anterior view) of an applied DRU-joint construction according to the invention.

DETAILED DESCRIPTION OF AN EMBODIMENT OF THE INVENTION

Figure 1:
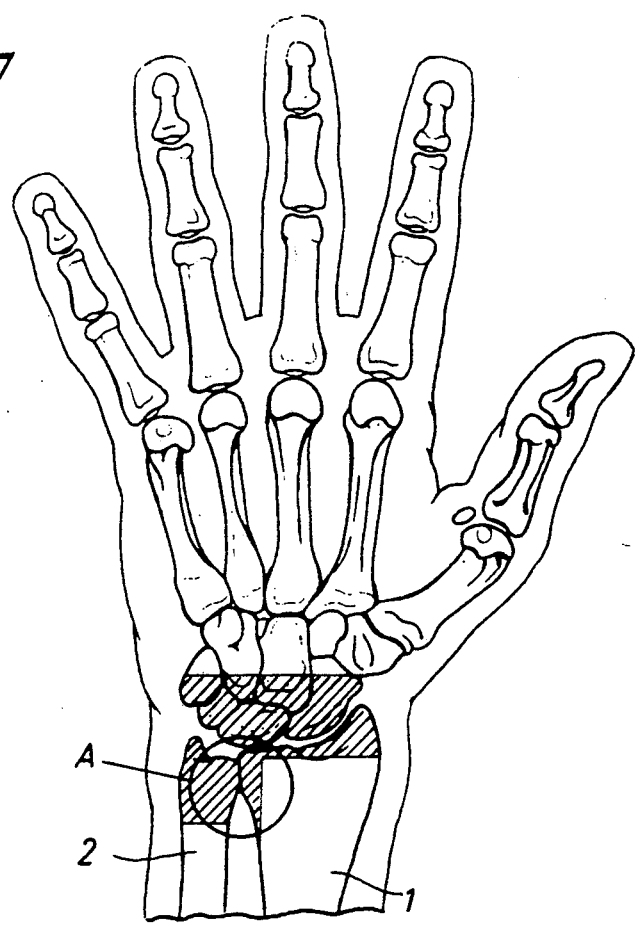
FIG. 1 is an anterior view showing the structure of a left wrist.

In FIG. 1 A denotes the area in a wrist constituting the distal radioulnar joint (DRU-joint). The joint provides the wrist with sufficient lateral rotation, achieved by this DRU-joint allowing the radius 1 to turn around the ulna 2. In a normal DRU-joint the rotation possible is approximately ±90°, i.e. 180°.

The artificial joint replacement for such a DRU-joint according to the invention comprises a guide body 3 with a borehole 4 running through it. However, the lower opening of the borehole 4 is somewhat smaller since the guide body 3 is provided at its lower end with an inwardly protruding end flange 5.

An insert 6 is applied in the borehole 4 of the guide body 3, its lower limiting surface 7 partially abutting the end flange 5. The height of the insert 6 is less than that of the borehole 4 and the insert is provided with a slot-shaped through-aperture 14 designed to displaceably (both laterally and vertically) hold a screwlike control element 8, the head 9 of said control element resting against the upper contact surface 10 of the slot 14 and a smooth section 12 adjoining the head 9 being located internally in the insert 6. The downward-facing portion of the head 9 may be generally hemispherical to match a corresponding curved shape of the upper contact surface 10, at and surrounding the slot 14. Below the smooth section 12 of the control element 8 is mounted a foot 19 which cooperates with the head 9 to hold the control element 8 vertically in position with respect to the slot 14. The upward-facing portion of the foot 19 may be generally hemispherical to match a corresponding curved shape of the lower contact surface 20, at and surrounding the slot 14. The control element 8 is provided with a lower, threaded portion 11, by means of which the element shall be secured in an anchoring element 13 implanted in a manner known per se in the ulna 2, said anchoring element being provided with an upper thread arrangement into which the lower, threaded portion 11 of the control element 8 is screwed. Stop nuts 15 or the like may be used in known manner to ensure that the element is screwed in to a suitable depth.

Figure 2:
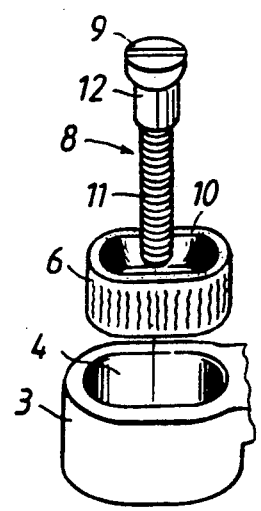

The mechanism shown in FIGS. 2 and 3 permits controlled displacement of the control element 8 in both lateral direction (through the slot-shaped through-aperture 14 in the insert 6) (toward the left and right as seen in FIG. 4) and vertical direction (limited by the position of the stop nuts). This arrangement results in a joint function substantially corresponding to the joint function of a normal DRU-joint, i.e. the arrangement permits the wrist to rotate approximately ±90°, i.e. approximately 180°.

The guide body 3 itself may suitably be secured along the outside of the radius 1, for instance via an extension 16 protruding from the guide body 3 and being provided with apertures for a number of anchoring screws 17 designed to be screwed into the radius in known manner, in principle transverse to the longitudinal direction of the bone.

All the parts in the construction described above, except for the insert 6, consist of a biocompatible material, preferably titanium. The insert 6 suitables consists of high-density polyethylene or some other suitable material.

However, the invention is not limited to the embodiments shown in the drawings but can be varied in many ways within the scope of the appended claims.

I claim:

1. System for reconstructing the distal radioulnar joint in a wrist, the system comprising:
    a guide body configured and sized for being anchored to the radius and ulna; means for anchoring the guide body to the radius and above the ulna;
    the guide body having a guide slot defined in it for guiding motion of a control element and an aperture formed in a bottom surface thereof;
    a control element extending through the guide slot in the guide body and through the aperture is the bottom surface of the guide body; means for securing the control element in the ulna;

the guide slot and the control element being configured to permit the control element to move both laterally in the guide slot with respect to the radius and vertically with respect to the radius.

2. The system of claim 1, wherein the control element is secured adjustably in the ulna.

3. The system of claim 2, wherein the guide body has a borehole therein, the borehole having an opening of a size permitting the control element to move laterally in the borehole;

the bottom of the guide body comprising an inwardly protruding end flange which defines an opening in the bottom of the guide body through which the control element extends toward the ulna.

4. The system of claim 3, further comprising an insert in the borehole in which the guide slot is defined, the insert at least partially abuts the end flange of the guide body, the insert having a height shorter than the height of the borehole and the guide slot being defined in the insert.

5. The system of claim 4, wherein the guide slot of the insert is shaped and positioned for holding the control element;

the control element including a head, the insert including an upper contact surface which is contacted by the control element head, the control element further having a smooth section which is beneath the head and which passes through the insert.

6. The system of claim 5, wherein the adjustable securement of the control element in the ulna is provided by a lower threaded portion of the control element; an anchoring element in the ulna, and the lower threaded portion being threadedly engaged with the anchoring element.

7. The system of claim 3, further comprising an insert in the borehole, and the guide slot being defined in the insert.

8. The system of claim 7, wherein the insert is comprised of high-density polyethylene.

9. The system of claim 2, wherein the adjustable securement of the control element in the ulna is provided by a lower threaded portion of the control element; an anchoring element in the ulna, and the lower threaded portion being threadedly engaged with the anchoring element.

10. The system of claim 3, wherein the means for anchoring the guide body to the radius comprise screw-like anchoring members extending from the guide body into the radius.

11. The system of claim 2, wherein the means for anchoring the guide body to the radius comprise screw-like anchoring members extending from the guide body into the radius.

12. The system of claim 11, wherein the guide body includes a protruding extension including apertures for the screw-like anchoring members to pass through and the screw-like anchoring members pass through the apertures and are screwed into the radius.

13. The system of claim 1, further comprising upper means for limiting downward vertical movement of the control element with respect to the guide slot.

14. The system of claim 13, wherein the upper means is a head on the control element which engages an upper contact surface of the guide body.

15. The system of claim 14, wherein said upper contact surface and said head have matching engaging surfaces.

16. The system of claim 1, further comprising lower means for limiting upward vertical movement of the control element with respect to the guide slot.

17. The system of claim 16, wherein the lower means is a foot on the control element which engages a lower contact surface of the guide body.

18. The system of claim 17, wherein said lower contact surface and said head have matching engaging surfaces.

19. The system of claim 5, wherein the control element further comprises a foot which engages a lower contact surface on the insert.

20. The system of claim 2, further comprising means for limiting both upward and downward movement while permitting lateral movement of the control member with respect to the guide slot.

21. The system of claim 1, further comprising an insert in the guide body, and the guide slot being defined in the insert.

22. The system of claim 2, further comprising an insert in the guide body, and the guide slot being defined in the insert.

* * * * *